United States Patent [19]

Gosser

[11] 4,255,343
[45] Mar. 10, 1981

[54] PREPARATION OF 2-T-ALKYLANTHRACENE

[75] Inventor: Lawrence W. Gosser, Wilmington, Del.

[73] Assignee: E. I. Du Pont de Nemours and Company, Wilmington, Del.

[21] Appl. No.: 65,862

[22] Filed: Aug. 13, 1979

[51] Int. Cl.³ .................... C07C 45/28; C07C 50/18; C07C 2/64; C07C 2/66
[52] U.S. Cl. .................... 260/385; 585/455; 585/458
[58] Field of Search .............. 585/455, 458; 260/385, 260/369

[56] References Cited

U.S. PATENT DOCUMENTS

| | | | |
|---|---|---|---|
| 1,685,635 | 9/1928 | Jaeger | 260/385 |
| 2,014,766 | 4/1934 | Isham | 585/458 |
| 3,251,897 | 5/1966 | Wise | 585/455 |
| 3,277,196 | 10/1976 | Winkler | 260/671 |
| 3,564,036 | 7/1971 | Miller et al. | 260/413 |
| 3,739,039 | 6/1973 | Boggs | 260/671 |
| 3,962,365 | 6/1976 | Gaydos et al. | 585/458 |

FOREIGN PATENT DOCUMENTS 1543144 9/1968 France .

OTHER PUBLICATIONS

*Compt. Read* vol. 216, p. 381, Buc-Hai et al., "The Use of Cyclohexene in the Synthesis of Aromatic Polynuclear Hydrocarbons", 1943.
*Monatsh Chem.* vol. 23, p. 672, "on Dibenzylanthracene" 1902, Lippman & Pollak.
*Chemical Abstracts* vol. 58 #4488a, Porshakova et al., "Alkylation of Anthracene with Alcohols in the Presence of Zinc Chloride", 1962.
*Chemical Abstracts,* vol. 33 #5812, Gindin et al., "Oxidation of Alkyl Anthracenes Alkylanthraquinones and Their Derivatives", 1938.
*J. Org. Chem.* vol. 42 #14, pp. 2407-2410, Fu & Harvey "Synthesis and Rearrangement of Tert-Butylanthracenes", 1977.
*J. Am. Chem. Soc.,* vol. 61, p. 1010, Calcott et al., "Hydrofluoric acid as a Condensing Agent", 1939.

*Primary Examiner*—Winston A. Douglas
*Assistant Examiner*—Raymond K. Covington

[57] ABSTRACT

Process for preparing 2-t-alkylanthracene, which process comprises contacting and reacting, with good mixing, at a temperature of at least 110° C., anthracene and a branched-chain alkylating agent, the alkylating moiety of which contains at least four carbon atoms, in the presence of a catalyst selected from hydrocarbonsulfonic acids which are free of nonaromatic unsaturation, organic carboxylic acids having a $K_a$ of 0.6 to 0.001, acid zeolites, amorphous silica-aluminas, and polymeric arenesulfonic acid resins, to give a product mixture of which the major constituent is 2-t-alkylanthracene.

14 Claims, No Drawings

4,255,343

PREPARATION OF 2-T-ALKYLANTHRACENE

DESCRIPTION

1. Technical Field

This invention relates to the preparation of 2-t-alkylanthracene by an acid-catalyzed alkylation of anthracene. Since 2-t-alkylanthracene can be readily oxidized to the corresponding 2-t-alkylanthraquinone, using known techniques, the alkylation process of the invention opens the way for, and can be the key step in, the preparation of 2-t-alkylanthraquinone which is a valuable intermediate in the production of hydrogen peroxide.

2. Background Art

The use of alkyl-substituted anthraquinones and their tetrahydro derivatives in cyclic processes for the production of hydrogen peroxide is well known. Particularly useful intermediates in such processes are 2-t-butylanthraquinone and 2-t-pentylanthraquinone. Known methods for preparing these intermediates generally involve a plurality of steps and, in many cases, are difficult and/or costly to carry out. Fu and Harvey, J. Org. Chem., 42, 2407 (1977), disclose the reaction of t-butyl alcohol and anthracene in the presence of trifluoroacetic acid, with 2,6-di-t-butylanthracene being formed virtually quantitatively, even under conditions designed to promote formation of the monosubstituted 2-t-butyl derivative.

It is an object of this invention to provide a process whereby anthracene is monoalkylated to a 2-t-alkylanthracene, wherein the alkyl group contains at least four carbon atoms, the 2-t-alkylanthracene thus produced being useful as an intermediate in the production of a 2-t-alkylanthraquinone, including the butyl- and pentylanthraquinones, using known oxidation techniques. Another object is to provide an improved two-step route to 2-t-butylanthraquinone and 2-t-pentylanthraquinone. Other objects will become apparent hereinafter.

DISCLOSURE OF THE INVENTION

For further comprehension of the invention, and of the objects and advantages thereof, reference may be had to the following description and to the appended claims in which the various novel features of the invention are more particularly set forth.

The present invention resides in a simple straightforward method for preparing 2-t-alkylanthracenes in good yield and with good selectivity from anthracene and readily available alkylating agents in the presence of relatively noncorrosive catalysts. Since the 2-t-alkylanthracene produced can be oxidized to the corresponding anthraquinone by known methods, the invention process makes possible an efficient two-step synthesis of valuable intermediates for use in the production of hydrogen peroxide.

The alkylation process of the invention consists in reacting anthracene and a branched-chain alkylating agent, the alkylating moiety of which contains at least four carbon atoms, at a temperature of at least about 110° C., in the presence of at least a catalytic amount of a catalyst selected from a hydrocarbonsulfonic acid which is free of nonaromatic unsaturation, an organic carboxylic acid having a $K_a$ of 0.6 to 0.001, an acid zeolite, an amorphous silica-alumina, or a polymeric arenesulfonic acid resin. The major (the preferred) product is a 2-t-alkylanthracene, that is, monoalkylated anthracene in which the alkyl group has the same number of carbon atoms as the alkylating moiety of the alkylating agent.

The alkylating agent can be any branchedchain compound, having at least four carbon atoms, that can be converted to a carbonium-ion species by contact with a strong acid. Such compounds include olefins, alcohols, and ethers and carboxylic acid esters derived from alcohols. Thus, for the production of 2-t-butylanthracene the alkylating agent can be, for example, isobutylene, isobutyl alcohol, t-butylalcohol, t-butyl methyl ether, di-t-butyl ether, t-butyl acetate, or isobutyl propionate. For the production of 2-t-pentylanthracene, the alkylating agent can be, for example, 2-methyl-1-butene, 2-methyl-2-butene, 3-methyl-1-butene, 2-methyl-1-butanol, 2-methyl-2-butanol (t-pentyl alcohol), 3-methyl-1-butanol, 3-methyl-2-butanol, methyl-t-pentyl ether, 3-methyl-1-butyl formate, or t-pentyl acetate.

Other considerations may apply to alkylation with compounds, the alkylating moieties of which each contain six or more carbon atoms. More specifically, whereas the t-butyl and t-pentyl groups do not exhibit isomerism, three isomers may be written for the t-hexyl group. Moreover, the number of isomers increases with further increasing number of carbon atoms. It is obvious, therefore, that alkylation with compounds containing six or more carbon atoms provides a mixture of products, that is, a mixture of alkylanthracenes containing different structural types of alkyl groups. However, the alkyl substituents are substantially all tertiary and in the 2-position. More specifically, experimental evidence suggests, for example, that substantially the same mixture of 2-t-hexylanthracenes is formed from any of the $C_6$ alkylating agents 2-methyl-2-pentane, 2-ethyl-1-butanol, 4-methyl-2-pentanol, and 3-methyl-3-pentanol. Because of their ready availability and because each provides only one type of t-alkyl group, the $C_4$ and $C_5$ alkylating agents are preferred.

Of the various functional types of alkylating agents operable herein, olefins and alcohols are preferred because of their ready availability. Olefins are especially preferred, since no hydroxyl-group-containing compounds are present or are formed when they are used in the alkylation process. Hydroxyl-group-containing compounds tend to lower the activity of some of the catalysts, particularly the zeolites, and may contribute to corrosion of any metal equipment used in the process.

The catalysts which are useful herein and which are selected from hydrocarbonsulfonic acids which are free of nonaromatic unsaturation include alkane-sulfonic acids, cycloalkanesulfonic acids, aralkane-sulfonic acids, and arenesulfonic acids, all of which are described by Suter in "The Organic Chemistry of Sulfur" (Wiley, 1943). Alkanesulfonic acids and their properties and uses are further described by Proell et al, Ind. Eng. Chem., 40, 1129 (1948). Examples of hydrocarbonsulfonic acids which are operable herein include methanesulfonic, ethanesulfonic, 2-butanesulfonic, 3-methylbutanesulfonic, hexanesulfonic, dodecanesulfonic, cyclohexanesulfonic, phenylmethanesulfonic, benzenesulfonic, toluenesulfonic, xylenesulfonic, and naphthalenesulfonic acids. Readily available mixtures, such as the $C_1$–$C_4$ alkanesulfonic acids discussed by Proell et al, can be used.

Organic carboxylic acids with the requisite $K_a$ are, for the most part, represented by the alkanoic acids containing one or more halogen substituents on the alpha carbon atoms. Examples include trifluoroacetic acid ($K_a$ of 0.59) and the chloroacetic acids ($K_a$ of 0.0014, 0.051, and 0.12). Although Fu and Harvey, loc cit., disclose the use of trifluoroacetic acid with anthracene and t-butyl alcohol, all operable herein, the reaction conditions of the invention process are not disclosed; hence, these authors obtain, principally, the dialkylated anthracene.

Acid zeolites, amorphous silica-aluminas, and polymeric arenesulfonic acid resins are well-known readily available materials that are described in the literature.

The preferred catalysts are methanesulfonic acid, acid zeolites, and amorphous silica-aluminas, because of their ready availabilities and relatively high activities and because they can readily be removed from the product mixture upon completion of the reaction. Methanesulfonic acid is relatively volatile (bp 167° C./10 mm) and can be distilled off below the boiling point of the alkylanthracene. The zeolites and silica-aluminas, which are insoluble in the reaction mixture, can be separated by filtration.

Reactant ratio, catalyst concentration, presence or absence of a diluent, temperature, and time are, to a substantial extent, interrelated. Adjustments thereof may be made to optimize the results achieved, so long as the adjustments are within the limits of the reaction conditions specified herein.

The alkylating agent/anthracene molar ratio is not unduly critical and can vary widely, for example, within the range 0.5 to 8. Ratios less than 0.5 may be acceptable, under a proper set of overall conditions. Ratios higher than 8 increase the rate of reaction and the conversion of anthracene, but such ratios may result in "overalkylation", with the formation of di- and sometimes trialkylated products. The preferred ratio is 0.6 to 2.2, more preferably 0.8 to 1.2.

The amount of hydrocarbonsulfonic acid in the alkylation reaction mixture can be, on a weight basis, 1 to 200% of the anthracene. No particular advantage results from the use of large quantities of this catalyst. The usual concentration is 5 to 20%. When a haloalkanoic acid is employed as the catalyst, the usual concentration is somewhat higher than 5 to 20%. With an acid zeolite, amorphous silica-alumina, or polymeric arenesulfonic acid resin, all of which are insoluble in the reaction mixture, as the catalyst, the minimum amount is about 0.5%, and the usual operating concentration is 2 to 20%. Larger quantities can be used but no particular advantage is provided.

Good mixing to promote intimate contact between the reactants and the catalyst is essential to obtaining the desired product, particularly if the reactants are present in more than one phase. Such mixing can be promoted, for example, by increasing the reaction temperature, by using more efficient agitation and, in some cases, by using an inert diluent. A diluent is not essential, however, and the process can take place in the absence of such a material, as exemplified hereinafter. Useful diluents include long chain alkanes, such as dodecane, and halogenated benzenes, such as trichlorobenzene.

The reaction temperature, in particular, depends on the alkylating agent, the mole ratio of reactants, the catalyst and its concentration, and whether a diluent is present. Temperatures as low as 110° C. suffice or some embodiments of the process. There is usually no advantage in exceeding 230° C. For most embodiments the preferred range is 140°–210° C., more preferably 150°–200° C.

The process is advantageously carried out at the autogenous pressure of a closed system containing the reactants, catalyst and diluent, if any. A closed system is particularly important when the alkylating agent is an olefin which has a boiling point well below the process temperature. Use of a closed system also permits easy variation of reaction temperature. If the alkylating agent has a sufficiently high boiling point, the process can be carried out in an open system at reflux temperature.

After completion of the reaction, solid catalyst can be separated from the reaction mixture by filtration. As shown in the examples, conversion, yield and product distribution can be determined analytically by means of gas chromatography and mass spectrometry. Actual separation of components of the product mixture can be made by conventional methods, such as distillation and preparative-scale gas chromatography.

The significance of the process of this invention is readily apparent from the following table wherein are shown data of Examples 1 to 10 and 12 to 18 and Experiments 1 to 5. Column A in the table shows the percentages, in the products, of the desired 2-t-alkylanthracene; column B, the percentages of all other alkylated anthracenes produced; column C, the ratios A/B; and column D, the percentages of unconverted anthracene recoverable. The data provided in columns C and D clearly show the superiority of the invention process, as reflected by said examples, over processes of the prior art, as reflected by Experiments 1 to 5, in that, in said examples, the ratios of the percentages of desired 2-t-alkylanthracenes to the percentages of other alkylated anthracenes are significantly higher. In general, by means of the process of this invention, ratios A/B of at least about 2 can be achieved, preferably at least about 3. It is to be understood that any unconverted anthracene can be recycled.

The significance of the process of the invention is further demonstrated by a consideration of the usefulness of 2-t-alkylanthracenes in the synthesis of hydrogen peroxide using known techniques wherein the anthracene is first oxidized to the anthraquinone. As shown in some of the examples, the process of the invention may yield 2-t-alkylanthracenes wherein the alkyl group is different from that of the alkylating agent. More specifically, if it is presumed that degradation of the alkylating agent takes place during the reaction so as to provide a different alkylating agent, the newly-formed alkylating agent may participate in the reaction and provide additional 2-t-alkyl-substituted product. Albeit the fact that the alkyl group in such a product is not the same as that in the starting alkylating agent, the product is still useful in the peroxide forming process in that it has a 2-t-alkyl group. Column E in the following table shows the total percentages of 2-t-alkylanthracenes produced; column F, the percentages of alkylated anthracenes other than 2-t-monoalkyl derivatives; and column G, the ratios E/F. In general, by means of the process of this invention, ratios E/F of at least about 3 can be achieved, preferably at least about 4.

TABLE

| Example | A | B | C | D | E | F | G |
|---|---|---|---|---|---|---|---|
| 1 | 52 | 10 | 5.2 | 38 | 52 | — | — |
| 2 | 50 | 8 | 6.3 | 38 | 50 | — | — |
| 3 | 3.9 | 1.3 | 3.0 | 94 | 5.2 | — | — |

TABLE-continued

| Example | A | B | C | D | E | F | G |
|---|---|---|---|---|---|---|---|
| 4 | 9.6 | 1.9 | 5.1 | 87 | 11.5 | — | — |
| 5 | 12.4 | — | — | 84 | 12.4 | — | — |
| 6 | 10 | 7.5 | 1.3 | 82 | 13.6 | 3.9 | 3.5 |
| 7 | 41 | 14.2 | 2.9 | 42 | 44.9 | 10.3 | 4.4 |
| 8 | 57 | 14.3 | 4.0 | 24 | 59 | 12.3 | 4.8 |
| 9 | 34 | 9.4 | 3.6 | 56 | 36.1 | 7.3 | 4.9 |
| 10 | 17 | 10.2 | 1.7 | 70 | 24.2 | 3 | 8.1 |
| 12 | 13 | — | — | 87 | 13 | — | — |
| 13 | 27 | 3 | 9 | 69 | 27 | 3 | 9 |
| 14 | 25 | 13 | 1.9 | 64 | 30 | 8 | 3.8 |
| 15 | 33 | 9 | 3.7 | 58 | 37 | 5 | 7.4 |
| 16 | 31 | 13.7 | 2.3 | 46 | 33.6 | 11.1 | 3.0 |
| 17 | 15 | 2 | 7.5 | 80 | 16 | 1 | 16 |
| 18 | 39 | 11 | 3.5 | 47 | 39 | 11 | 3.5 |
| Experiment | | | | | | | |
| 1 | 14 | 77 | 0.18 | 0 | 26 | — | — |
| 2 | 27 | 30 | 0.9 | 38 | 32.5 | — | — |
| 3 | 24 | 14 | 1.7 | 60 | 26 | — | — |
| 4 | 17 | 25 | 0.68 | 52 | 19 | — | — |
| 5 | 40 | 36 | 1.1 | 22 | 47 | — | — |

A: % 2-t-Monoalkyl* Anthracene
B: % All Other Alkylated Anthracenes
C: A/B
D: % Unconverted Anthracene
E: Total % 2-t-Monoalkyl** Anthracene
F: % Alkylated Anthracenes Other Than 2-t-Monoalkyl
G: E/F
*wherein the alkyl group has the same number of carbon atoms as the alkylating moiety of the alkylating agent
**includes all 2-t-monoalkyl groups In a further comparison of the invention process and prior art processes using the ZnCl$_2$/HCl catalyst system, the latter system is much more corrosive to metal apparatus than the catalysts of the present invention and requires the disposal (and loss) or recovery of large amounts of ZnCl$_2$. The ZnCl$_2$ cannot be removed simply by filtration, as can the acid zeolite, amorphous silica-alumina, and polymeric arenesulfonic acid resin catalysts of this invention process, nor can it be removed by distillation below the boiling point of the alkylanthracene, as can a hydrocarbonsulfonic acid catalyst such as methanesulfonic acid of the invention process, since it is less volatile. In addition, if a product mixture containing ZnCl$_2$/HCl is distilled, the presence of the catalyst may lead to loss of desired product during distillation, for example, by resinification.

The following experiments are included as being representative of prior art on the formation of alkylanthracenes and on the formation of alkylanthraquinones, the latter using alkylanthracenes that are products of the process of this invention as starting materials. Experiments 1 to 5 were carried out substantially according to the procedure of Porshakova and Kuchkarev, Uzbeksk, Khim. Zh., 6, No. 2, 51 (1962), as abstracted in Chemical Abstracts, 58, 4488g (1963). In Experiment 1 the mole ratio of alkylating agent (3-methyl-1-butanol) to anthracene is 10 to 1. This relatively high ratio would be expected to favor the formation of di- and polyalkylated anthracenes. In Experiments 2 to 5 the effect of lower mole ratios was studied. The ratio was 2.1/1 in Experiments 2, 3 and 4 and 3.4/1 in Experiment 5.

Experiment 6 was carried out using 2-t-butylanthracene, a product of the process of this invention, as starting material. Experiment 7 was carried out using the distillate of Example 8, a mixture of 2-t-pentylanthracene and anthracene, as starting material.

EXPERIMENT 1

A mixture of 46 g of zinc chloride and 5 ml of 3-methyl-1-butanol was charged to a round-bottom flask equipped with a stirrer, reflux condenser, and gas-addition tube. The flask was partly immersed in an oil bath at 150°–152° C., and gaseous hydrogen chloride was allowed to flow through the flask. A suspension of 12 g of powdered anthracene in 68 ml of 3-methyl-1-butanol was prepared. An 8-ml portion of this suspension was added to the stirred mixture in the reaction flask about every 20 minutes over a period of 3 hours. The heating and stirring were continued for 15 minutes after the last addition; the mixture then was cooled to room temperature and diluted with 200 ml of water, 10 ml of concentrated hydrochloric acid, and 800 ml of methylene chloride. The methylene chloride layer was separated, washed sequentially with two 400-ml portions of water and with aqueous sodium bicarbonate, and dried over anhydrous magnesium sulfate. Gc analysis as in Example 3 showed that this solution included butylanthracene, pentylanthracene, dibutylanthracene, butylpentylanthracene, and dipentylanthracene, with little or no unreacted anthracene. Gc peaks were identified by gc/mas spec analysis on a sample from another experiment on half the scale described above. The solution was concentrated by distillation up to 145° C. (40 mm), to give 30.6 g of undistilled material. On further distillation, 5.1 g of distillate were collected up to an oil-bath temperature of 260° C. (10 mm). Gc analysis of this sample showed that it was composed principally of materials with retention times lower than that of anthracene. Distillation was continued, and 22.9 g of distillate were collected to a pot temperature of about 360° C. (0.1 mm). At this point only 1.7 g remained undistilled. Gc analysis as in Example 3 indicated little or no anthracene and about 12% butylanthracene, 14% pentylanthracene, 14% dibutylanthracene, 30% butylpentylanthracene, and 21% dipentylanthracene. The gc trace of this product was qualitatively similar to that of the anthracene-alkylanthracene region in the original methylene chloride solution.

EXPERIMENT 2

A reactor of the type used in Experiment 1 was charged with a mixture of 4.6 g of zinc chloride and 0.5 ml of 3-methyl-1-butanol. The flask was heated in an oil bath at 150°–160° C. and charged with 1.2 g of anthracene and an additional 1 ml of 3-methyl-1-butanol. The reactor was swept with gaseous hydrogen chloride, and the mixture was stirred for ½ hour at 150°–160° C. It was then cooled and worked up with methylene chloride and aqueous hydrochloric acid as in Experiment 1, with appropriate reductions in volumes. Gc analysis of the methylene chloride solution as in Example 3 indicated 38% anthracene, 5.5% butylanthracene, 27% pentylanthracene, 1% dibutylanthracene, 7% butylpentylanthracene, and 17% dipentylanthracene. The $^1$H nmr spectrum of the mixture obtained after distilling off methylene chloride and other volatile materials indicated that the butyl and pentyl substituents were primarily tertiary, with possibly a minor amount of secondary alkyl groups also being present.

EXPERIMENT 3

Experiment 2 was repeated, except that 1 ml of 1,2,4-trichlorobenzene was added with the original charge. Gc analysis as in Example 3 indicated 60% anthracene, 2.0% butylanthracene, 24% pentylanthracene, 0.6% dibutylanthracene, 3.1% butylpentylanthracene, and 8.7% dipentylanthracene.

EXPERIMENT 4

Experiment 2 was repeated, except that 2 ml, instead of 1 ml, of 3-methyl-1-butanol was added with the anthracene. Gc analysis as in Example 3 indicated 52% anthracene, 1.7% butylanthracene, 17% pentylanthracene, 1.1% dibutylanthracene, 6.0% butylpentylanthracene, and 16% dipentylanthracene.

EXPERIMENT 5

A mixture of 1.2 g of anthracene, 14 g of zinc chloride, 9 ml of decane, and 0.5 ml of 3-methyl-1-butanol was charged to a reactor of the type used in Experiment 1. The system was swept with gaseous hydrogen chloride and heated in an oil bath at 154° C. An additional 1 ml of 3-methyl-1-butanol was added, the reactor was swept again with gaseous hydrogen chloride, and the mixture was stirred and heated for ½ hour. It was worked up by the method of Experiment 2. Gc analysis as in Example 3 indicated 22% anthracene, 7.0% butylanthracene, 40% pentylanthracene, 1.0% dibutylanthracene, 8.6% butylpentylanthracene, and 19% dipentylanthracene.

EXPERIMENT 6

A mixture of 0.20 g of 2-t-butylanthracene, 1 mg of vanadium pentoxide, 160 mg of sodium chlorate, 2 ml of acetic acid, and 0.4 ml of aqueous 2% sulfuric acid was heated to boiling and refluxed for about two minutes. Water (10 ml) was added, the mixture was extracted with two 2 ml portions of methylene chloride, and the combined extracts were washed sequentially with water and with aqueous sodium bicarbonate, and dried over anhydrous magnesium sulfate. Analysis was by gc as in Example 3 and showed 14% 2-t-butylanthracene, 702-t-butylanthraquinone, 8% di-t-butylanthracene, and 6% tri-t-butylanthracene. The peak assignments were confirmed by gc/mas spec. This experiment shows that a 2-t-alkylanthracene can be readily oxidized to the corresponding 2-t-alkylanthraquinone without oxidation of the side chain and with only a minor amount of redistribution of alkyl groups.

EXPERIMENT 7

A mixture of 0.50 g of the distillate from the second part of Example 8, 1 mg of vanadium pentoxide, and 1 ml of acetic acid was heated with magnetic stirring in an oil bath at 120° C. while 0.50 g of sodium chlorate was added in 0.1 g portions over 5 minutes. After heating for 15 minutes more, the mixture was cooled and diluted with 20 ml of methylene chloride. The solution was washed sequentially with water and with aqueous sodium bicarbonate solution and dried over anhydrous magnesium sulfate. After evaporating off volatile materials 0.5 g of an orange oil was recovered. The $^1$H nmr spectrum indicated a mixture consisting principally of 2-t-pentylanthraquinone and anthraquinone. Gc analysis as in Example 3 indicated 21% anthraquinone, 69% 2-t-pentylanthraquinone, and 2.4% dialkylanthraquinones.

The following examples are representative of the process of the invention. Examples 1 to 5 demonstrate the use of various alkylating agents and zeolite catalysts; Examples 6 to 11 and 18, the use of various alkylating agents and methanesulfonic acid as catalysts; Examples 3, 4, 7, and 12 to 17, the use of 2-methyl-2-butene as alkylating agent and various catalysts; Examples 3 and 4, the use of the same alkylating agent and the same catalyst, but with different treatments of the catalyst; and Examples 6 and 8, the use of the same alkylating agent and the same catalyst, but in different diluents.

EXAMPLE 1

A mixture of 0.5 g of zeolite (Linde Catalyst Base 32-300; a thermally stabilized powder form of Linde Type Y Molecular Sieve) that had been heated at 700° C. in air and then stored and handled under ambient conditions, 0.5 g of anthracene, and 1 ml of t-butyl alcohol was placed in a metal autoclave, the autoclave was sealed, and the mixture was heated at 230° C. for 1 hour with shaking and then cooled. It was analyzed by gas chromatography on a 3.175 mm × 2.44 m SE 30 column with a thermal-conductivity detector. The peak areas were determined by computer processing of the detector output. The compounds corresponding to the peaks were identified by gc (gas chromatography)/mass spec (mass spectrometry) and by comparing retention times with those of known materials under the same instrument conditions. The areas of peaks at solvent-retention times were eliminated, and the percentages of materials in the rest of the mixture were calculated manually. The relative area percents of peaks in the retention-time region of anthracene to tributylanthracene were as follows: 38% anthracene, 52% butylanthracene (substantially 2-t-butyl-), and 10% dibutylanthracene(s). For compounds such as these (having substantial molecular weights and relatively low volatilities) the relative areas generally correspond closely to the relative weights of the compounds in the mixture.

EXAMPLE 2

Example 1 was repeated, except that 1 g of isobutyiene was used in place of 1 ml of t-butyl alcohol and 0.5 g of a different zeolite (Linde Catalyst Base 33-200; an ammonium ion-exchanged powder form of Linde 32-300) was used. Gc analysis of the product mixture indicated 38% anthracene, 50% butylanthracene, and 8% dibutylanthracene(s). Analysis by nmr (nuclear magnetic resonance) of the products of another experiment using the same reactants showed that the butylanthracene was substantially all 2-t-butylanthracene.

EXAMPLE 3

A mixture of 0.50 g of anthracene, 0.50 g of zeolite 33-200, 0.50 ml of 2-methyl-2-butene, and 0.50 ml of dodecane was heated at 230° C. for 2 hours in a metal shaker tube. Gc analysis of the product mixture was as in Example 1, except that peaks at solvent-retention times were excluded by the computer, and the relative area percents were calculated by the computer. Peak assignments were confirmed by gc/mass spec. The analysis indicated 94% anthracene, 1.3% 2-t-butylanthracene, 3.9% pentylanthracene. Analysis by nmr of the products of a later experiment using the same reactants showed that the pentylanthracene was substantially all 2-t-pentylanthracene.

EXAMPLE 4

A mixture of 0.20 g of zeolite 33-200 that had been calcined at 600° C. and kept dry, 0.20 g of anthracene, 1.0 ml of dodecane, and 0.10 ml of 2-methyl-2-butene in a glass vial with a rubber septum was heated for about 10 minutes in an oil bath at 177° C. Analysis of the product mixture by gc as in Example 3 indicated 87% anthracene, 1.9% 2-t-butylanthracene, and 9.6% pentylanthracene. The presence of pentylanthracene was confirmed by gc/mass spec analysis. Analysis by nmr of the products of a later experiment using the same reactants showed that the pentylanthracene was substantially all 2-t-pentylanthracene. Even under the milder conditions of reaction, more pentylanthracene is formed than in Example 4, demonstrating the improvement achieved when the catalyst is kept particularly dry before use.

EXAMPLE 5

Example 4 was repeated, except that 0.10 ml of 2-methyl-1-butanol was used in place of 0.10 ml of 2-methyl-2-butene. Gc analysis of the product mixture as in Example 3 indicated 84% anthracene and 12.4% pentylanthracene. The pentylanthracene was shown to be substantially all 2-t-pentylanthracene following nmr analysis in a later experiment.

EXAMPLE 6

A mixture of 0.10 g of anthracene, 1.0 ml of dodecane, 0.05 ml of methanesulfonic acid, and 0.10 ml of 3-methyl-1-butanol in a glass vial with a rubber septum was heated in an oil bath at 205° C. for ½ hour. Gc analysis of the product mixture as in Example 3 indicated 82% anthracene, 3.6% 2-t-butylanthracene, 10% pentylanthracene, and 3.9% dialkylanthracenes. The pentylanthracene was shown to be substantially all 2-t-pentylanthracene following nmr analysis in a later experiment.

EXAMPLE 7

A mixture of 2.0 g of anthracene, 2.0 ml of 1,2,4-trichlorobenzene and 0.10 ml of methanesulfonic acid in a round-bottom flask with a rubber septum was heated with magnetic stirring for 33 minutes in an oil bath 165° C. while 0.90 ml of 2-methyl-2-butene was added through the septum from a syringe pump. Gc analysis of a small sample of the product mixture as in Example 3 indicated 42% anthracene, 3.9% 2-t-butylanthracene, 41% 2-t-pentylanthracene, 1.9% hexylanthracenes, and 8.4% dialkylanthracenes. Characterization of the pentylanthracene as 2-t-pentylanthracene was by nmr analysis of the distillate from the product mixture boiling in the anthracene-alkylanthracene region.

EXAMPLE 8

A mixture of 2.0 g of anthracene, 2.0 ml of 1,2,4-trichlorobenzene, and 1.0 ml of methanesulfonic acid in a round-bottom flask with a rubber septum was heated in an oil bath at 175° C. with magnetic stirring for ½ hour while 1.0 ml of 3-methyl-1-butanol was added through the septum from a syringe pump. Gc analysis of a small sample of the product mixture as in Example 3 indicated 24% anthracene, 2% 2-t-butylanthracene, 57% 2-t-pentylanthracene, 1.3% hexylanthracenes, and 11% dialkylanthracenes. The remainder of the product mixture was diluted with methylene chloride, and the solution was washed with a solution of 1 g of sodium hydroxide in 50 ml of water and then with water; it was dried over anhydrous magnesium sulfate. After evaporation of the methylene chloride, the mixture was vacuum-distilled, and 0.9 g of material boiling in the anthracene-alkylanthracene region was collected. The $^1$H nmr spectrum of the distillate indicated that it was mostly 2-t-pentylanthracene (68%) and anthracene (20%). These compounds can be separated by precision distillation.

EXAMPLE 9

A mixture of 0.10 g of anthracene, 1.0 ml of 1,2,4-trichlorobenzene, 0.10 ml of methanesulfonic acid, and 0.065 ml of t-butyl methyl ether in a glass vial with a rubber septum was heated for 15 minutes in an oil bath at 176° C. with shaking. Gc analysis of the product mixture as in Example 3 indicated 56% anthracene, 34% 2-t-butylanthracene, 2.1% 2-t-pentylanthracene, and 7.3% dibutylanthracene. These findings were confirmed by gc/mass spec analysis.

EXAMPLE 10

Example 9 was repeated, except that 0.085 ml of 3-methylbutyl acetate ("isoamyl" acetate) was used instead of 0.065 ml of t-butyl methyl ether. Gc analysis of the product mixture as in Example 3 indicated 70% anthracene, 4.5% 2-t-butylanthracene, 17% 2-t-pentylanthracene, 2.7% 2-t-hexylanthracene, and 3% dialkylanthracenes. These findings were confirmed by gc/mass spec analysis.

EXAMPLE 11

Example 9 was repeated, except that 0.125 ml of 2-methyl-1-undecene was used instead of 0.065 ml of t-butyl methyl ether. In gc analysis of the product mixture by the method of Example 3, a peak at long-retention time was shown by gc/mass spec to be dodecylanthracene. The product is believed to be substantially a mixture of 2-t-dodecylanthracenes.

EXAMPLE 12

Pellets of commercially available Davison 970 amorphous silica-alumina catalyst were crushed with a mortar and pestle. The powder was dried three hours in a 550° C. oven and kept under nitrogen. A mixture of 1.0 g of this dried catalyst, 2.0 g of anthracene, and 6 ml of 1,2,4-trichlorobenzene was prepared under nitrogen. The mixture was then heated with a 165° C. oil bath and stirred while 1.0 ml of 2-methyl-2-butene was added by syringe pump over one hour. The mixture was heated for 20 minutes more and cooled. Gc analysis as in Example 3 showed 87% unreacted anthracene and 13% 2-t-pentylanthracene.

EXAMPLE 13

A mixture of 0.5 g of anthracene, 0.10 g of p-toluenesulfonic acid monohydrate, and 1 ml of dodecane was placed with a magnetic stirring bar in a vial closed with a rubber septum. The mixture was heated with a 203° C. oil bath, and 0.2 ml of 2-methyl-2-butene was injected in four 0.05 ml portions in about 5minutes. Analysis by gc as in Example 3 showed 69% anthracene, 27% 2-t-pentylanthracene and 3% dialkylanthracenes.

EXAMPLE 14

A mixture of 3.0 g of anthracene, 1.5 g of Amberlyst ® 15, (Rohm & Haas commercially available macroreticular sulfonic acid cation-exchange resin), and 9 ml of 1,2,4-trichlorobenzene was placed in a flask with a magnetic stirring bar. The flask was closed with a rubber septum and heated with a 145° C. oil bath. A syringe pump was used to add 1.5 ml of 2-methyl-2-butene to the stirred mixture over 1.5 hours. Analysis by gc as in Example 1 indicated 64% anthracene, 5% 2-t- butylanthracene, 25% 2-t-pentylanthracene, 2% hexylanthracenes, and 6% dialkylanthracenes.

EXAMPLE 15

A mixture of 1.0 g of anthracene, 1.0 ml of trifluoroacetic acid, 1.0 ml of 1,2,4-trichlorobenzene and 0.50 ml of 2-methyl-2-butene was placed in a 10 ml metal autoclave. This was heated at 160° C. with shaking for ½ hour. Analysis by gc as in Example 3 showed 58% anthracene, 4% 2-t-butylanthracene, 33% 2-t-pentylanthracene, and 5% dialkylanthracenes.

EXAMPLE 16

A mixture of 0.30 g of anthracene and 2.3 g of trichloroacetic acid was placed in a test tube with a magnetic stirring bar. The tube was closed with a septum and heated in a 168°–173° C. oil bath. The addition of 0.3 ml of 2-methyl-2-butene was completed in about five minutes. The stirred mixture was left hot 15 minutes and then cooled and diluted with methylene chloride. The solution was washed with water and aqueous NaHCO$_3$ solution before analysis by gc as in Example 3. This indicated 46% anthracene, 2.6% 2-t-butylanthracene, 31% 2-t-pentylanthracene, and 11.1% dialkylanthracenes.

EXAMPLE 17

A mixture of 0.3 g of anthracene and 2.1 g of chloroacetic acid was placed in a test tube with a magnetic stirring bar, and the tube was closed with a septum. The stirred mixture was heated with a 200° C. oil bath as 0.4 ml of 2-methyl-2-butene was added in small portions during 10 minutes. The hot mixture was stirred an additional two hours. It was then cooled and worked up as in Example 16. The gc analysis as in Example 3 indicated 80% anthracene, 1% 2-t-butylanthracene, 15% 2-t-pentylanthracene, and 1% dialkylanthracenes.

EXAMPLE 18

A mixture of 2.0 g of anthracene, 2.0 ml of 1,2,4-trichlorobenzene, and 0.10 ml of methanesulfonic acid was placed in a flask with a magnetic stirring bar and septum closure. The stirred mixture was heated with a 170° C. oil bath while 1.0 ml of 2-methyl-2-pentene was added by syringe pump in ½ hour. Analysis by gc as in Example 3 indicated 47% anthracene, 39% 2-t-hexylanthracenes and 11% dialkylanthracenes. The $^1$H nmr was in accord with a mixture of anthracenes, each with a predominantly t-hexyl side chain in the 2-position.

The overall yield of 2-t-alkylanthracene can be increased significantly by isolating the dialkylanthracene fraction from the product mixture of the process of the invention and treating it under the alkylation conditions described above (including catalyst, diluent, temperature and pressure), either alone or in the presence of added anthracene. In the absence of anthracene, monoalkylanthracene is formed by dealkylation; in the presence of anthracene it is formed by transalkylation in addition to dealkylation. Neither the dealkylation nor the transalkylation can be brought about to a significant extent merely by heating the product mixture from the alkylation process of the invention for a longer period; that is, the dialkylanthracene fraction must first be isolated.

The process variables for the aforesaid dealkylation/transalkylation process are the same as those described above for the alkylation process, with the following appropriate changes: First, the molar ratio involved is that of the dialkylanthracene fraction to anthracene, when the latter is present. This ratio is not unduly critical and can vary between about 2 to 1 (2.0) and 1 to 2 (0.5), or even more widely. Usually, the ratio is approximately 1 to 1 (1.0). Second, the amount of catalyst in the reaction mixture is based on the weight of the dialkylanthracene, not the anthracene.

The following examples illustrate the dealkylation/transalkylation process.

The dialkylanthracene fraction used as starting material in each example was prepared as follows. Two batches of crude alkylation mixture were prepared by treating anthracene with 2-methyl-2-butene in the presence of methanesulfonic acid. They were combined, and the mixture was fractionally distilled under reduced pressure. The highest-boiling fraction was partly redistilled to give a distillate that was indicated by gc analysis to be mostly monopentylanthracene.

Analysis by gc of the undistilled residue from the second distillation indicated that its major volatile components were dipentylanthracene and butylpentylanthracene. Part of this residue was purified by chromatography on silica gel followed by crystallization from ethanol. Two samples of starting material prepared by this method were shown by gc analysis to contain about 90% dipentylanthracene, 8–9% butylpentylanthracene, about 1% hexylpentylanthracene, and a trace of monopentylanthracene. For Example 19 the dialkylanthracene prepared as described above was further purified by vacuum sublimation.

EXAMPLE 19

A mixture of 0.20 g of dialkylanthracene fraction, 0.30 ml of methanesulfonic acid, and 4 ml of 1,2,4-trichlorobenzene was heated with stirring for 30 minutes in an oil bath at 190° C. Analysis of the product mixture by gc showed it to contain about 27% pentylanthracene, 16% butylanthracene, 16% anthracene, 1% dihydroanthracene, 25% dipentylanthracene, 3% dibutylanthracene, 8.4% butylpentylanthracene, and 0.8% hexylpentylanthracene. The peak assignments were made on the basis of the retention times and the overall pattern of the gc trace compared with those of known mixtures. Analysis of the products of a similar run by nmr indicated that the pentylanthracene and butylanthracene were of the order of 90% of 2-t-pentylanthracene and 2-t-butylanthracene, respectively.

EXAMPLE 20

A mixture of 0.60 g of dialkylanthracene fraction, 0.30 g of anthracene, 0.1 g of methanesulfonic acid, and 1 ml of 1,2,4-trichlorobenzene was heated for 2 hours with stirring in an oil bath at 170° C. Analysis of the product mixture by gc, with calibration by fluorene as an internal standard and with response factors, indicated the presence of about 21.5% pentylanthracene, 1.8% butylanthracene, 23% anthracene, 50.1% dipentylanthracene (probably containing a small amount of hexylpentylanthracene), and 3.6% butypentylanthracene. The peak assignments were made as in Example 19.

EXAMPLE 21

A mixture of 1.0 g of dialkylanthracene fraction (the same starting material as in Example 20), 1.0 g of anthracene, 0.20 g of methanesulfonic acid, and 2.0 ml of 1,2,4-trichlorobenzene was heated for 1.5 hour with stirring in an oil bath at 170°–175° C. The cooled reaction mixture was diluted with 20 ml of methylene chloride, and the solution was extracted with 20 ml of water and then with 20 ml of aqueous saturated sodium bicarbonate. The solution was then filtered through anhydrous magnesium sulfite and analyzed by gc. The anthracene/alkylated anthracene mixture was indicated to contain 38% pentylanthracene (containing about 0.2% hexylanthracene), 3.4% butylanthracene (containing about 0.3% of an unknown component), 36% anthracene, 1.9% butylpentylanthracene, and 18% dipentylanthracene (containing about 0.3% hexylpentylanthracene). The peak assignments were confirmed by gc/mass spec.

EXAMPLE 22

A mixture of 2.0 g of dialkylanthracene fraction (the same starting material as in Example 20), 0.2 g of methanesulfonic acid, and 2.0 ml of 1,2,4-trichlorobenzene was heated with stirring and worked up and analyzed by the method of Example 21. Analysis indicated the presence of 19% pentylanthracene (containing about 0.4% hexylanthracenes), 2.6% butylanthracene, 1.3% anthracene, 64.7% dipentylanthracene (containing about 1.7% hexylpentylanthracenes), 1.3% dibutylanthracene, and 11% butylpentylanthracene.

Best Mode For Carrying Out the Invention

The best mode for carrying out the invention entails use of 2-methyl-2-butene as the alkylating agent, methanesulfonic acid as the catalyst, trichlorobenzene as the diluent and a reaction temperature of 150°–180° C. The best mode is exemplified by Example 7.

INDUSTRIAL APPLICABILITY

The process of the invention is applicable to the production of 2-t-alkylanthracene which can be readily oxidized, using known techniques, to the corresponding anthraquinone which is a valuable intermediate in the production of hydrogen peroxide.

I claim:

1. Process for preparing 2-t-alkylanthracene, which process comprises intimately contacting and reacting, at a temperature of at least 110° C., anthracene and a branched-chain alkylating agent, the alkylating moiety of which contains at least four carbon atoms, in the presence of a catalyst selected from hydrocarbonsulfonic acids which are free of non-aromatic unsaturation, organic carboxylic acids having a $K_a$ of 0.6 to 0.001, acid zeolites, amorphous silica-aluminas, and polymeric arenesulfonic acid resins, to give a product mixture of which the major constituent is 2-t-alkylanthracene.

2. Process of claim 1 wherein the temperature is 110°–230° C. and the alkylating agent is an olefin, an alcohol or an ether or carboxylic acid ester of an alcohol.

3. Process of claim 2 wherein the temperature is 140°–210° C. and the alkylating moiety is butyl or pentyl.

4. Process of claim 1 wherein the catalyst is a hydrocarbonsulfonic acid which is free of non-aromatic unsaturation.

5. Process of claim 4 wherein the catalyst is methanesulfonic acid.

6. Process of claim 1 wherein the catalyst is an acid zeolite.

7. Process of claim 6 wherein the zeolite is calcined and maintained dry before use in the process.

8. In a process of producing and then oxidizing 2-t-alkylanthracene to 2-t-alkylanthraquinone the improvement in combination therewith of producing the 2-t-alkylanthracene by the process of claim 1.

9. Process of claim 8 wherein the 2-t-alkylanthracene is 2-t-butylanthracene.

10. Process of claim 8 wherein the 2-t-alkylanthracene is 2-t-pentylanthracene.

11. Process of claim 1 wherein dialkylanthracene, which is a minor constituent is isolated from the product mixture and contacted with a catalyst selected from hydrocarbonsulfonic acids which are free of nonaromatic unsaturation, organic carboxylic acids having a $K_a$ of 0.6 to 0.001, acid zeolites, amorphous silica-aluminas, and polymeric arenesulfonic acid resins, at a temperature of at least 110° C., to give a product mixture containing 1-t-alkylanthracene.

12. Process of claim 11 which is carried out in the presence of anthracene.

13. Process of claim 11 wherein the catalyst is a hydrocarbonsulfonic acid which is free of nonaromatic unsaturation.

14. Process of claim 13 wherein the catalyst is methanesulfonic acid.

* * * * *